United States Patent
Venkatesh et al.

(10) Patent No.: US 10,368,753 B2
(45) Date of Patent: Aug. 6, 2019

(54) METHOD AND SYSTEM FOR DETERMINING STRAIN RELAXATION OF LEFT VENTRICULAR DIASTOLIC FUNCTION

(71) Applicant: THE JOHNS HOPKINS UNIVERSITY, Baltimore, MD (US)

(72) Inventors: Bharath Ambale Venkatesh, Baltimore, MD (US); Anderson Armstrong, Baltimore, MD (US); Joao A. C. Lima, Timonium, MD (US); Chia-Ying Liu, Ellicott City, MD (US); Boaz D. Rosen, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 1074 days.

(21) Appl. No.: 14/439,290

(22) PCT Filed: Nov. 1, 2013

(86) PCT No.: PCT/US2013/067957
§ 371 (c)(1),
(2) Date: Apr. 29, 2015

(87) PCT Pub. No.: WO2014/071126
PCT Pub. Date: May 8, 2014

(65) Prior Publication Data
US 2015/0289769 A1    Oct. 15, 2015

Related U.S. Application Data

(60) Provisional application No. 61/721,174, filed on Nov. 1, 2012.

(51) Int. Cl.
*A61B 5/00*    (2006.01)
*A61B 5/02*    (2006.01)
(Continued)

(52) U.S. Cl.
CPC .............. *A61B 5/02* (2013.01); *A61B 5/0044* (2013.01); *A61B 5/046* (2013.01); *A61B 5/0452* (2013.01);
(Continued)

(58) Field of Classification Search
CPC ......... G06F 19/00; G16H 50/30; A61B 8/485; A61B 8/0883; A61B 5/7282;
(Continued)

(56) References Cited

U.S. PATENT DOCUMENTS

2002/0072674 A1    6/2002    Criton et al.
2008/0285819 A1    11/2008    Konofagou et al.
(Continued)

FOREIGN PATENT DOCUMENTS

JP    2009-530010 A    8/2009
JP    2010-194299 A    9/2010

OTHER PUBLICATIONS

Cabrita et al. "Validation of the isovolumtric relaxation time for the estimation of pulmonary systolic arterial blood pressure in chronic pulmonary hypertension" European Heart Journal—Cardiovascular Imaging (May 15, 2012) 14, 51-55.*

*Primary Examiner* — Thomas J Hong
*Assistant Examiner* — Helene Bor
(74) *Attorney, Agent, or Firm* — Harrity & Harrity, LLP

(57) ABSTRACT

An embodiment in accordance with the present invention provides a system and method for determining cardiac events. The system and method include using an imaging modality to obtain a cardiac image of the subject. The image is then used to determine the subject's systolic, post-systolic, and early diastolic strain peaks. Additionally, a strain rate index (SRI) value is computed for the subject using the systolic, post-systolic, and early diastolic strain peaks. The SRI value can then be used to determine a level of risk of (Continued)

cardiac failure. Further, a likelihood of atrial fibrillation can also be determined. The SRI value and risk of cardiac event can then be used to create a treatment plan for the subject, if necessary.

20 Claims, 5 Drawing Sheets

(51) Int. Cl.
*A61B 8/08* (2006.01)
*A61B 5/046* (2006.01)
*A61B 5/055* (2006.01)
*G16H 50/30* (2018.01)
*A61B 5/0452* (2006.01)
*G06F 19/00* (2018.01)

(52) U.S. Cl.
CPC ............ *A61B 5/055* (2013.01); *A61B 5/7275* (2013.01); *A61B 5/7282* (2013.01); *A61B 8/0883* (2013.01); *A61B 8/485* (2013.01); *G06F 19/00* (2013.01); *G16H 50/30* (2018.01); *A61B 2576/023* (2013.01)

(58) Field of Classification Search
CPC ....... A61B 5/7275; A61B 5/055; A61B 5/046; A61B 5/0452; A61B 5/0044; A61B 5/02; A61B 2576/023
See application file for complete search history.

(56) References Cited

U.S. PATENT DOCUMENTS

| | | | |
|---|---|---|---|
| 2008/0294057 A1* | 11/2008 | Parlikar | A61B 5/021 600/481 |
| 2009/0209869 A1* | 8/2009 | Kovacs | A61B 5/0215 600/486 |
| 2010/0081937 A1 | 4/2010 | Hamilton | |
| 2010/0280366 A1* | 11/2010 | Arne | A61B 5/046 600/425 |

\* cited by examiner

METHOD AND SYSTEM FOR DETERMINING STRAIN RELAXATION OF LEFT VENTRICULAR DIASTOLIC FUNCTION

CROSS-REFERENCE TO RELATED APPLICATIONS

This application is a 35 U.S.C. § 371 U.S. national entry of International Application PCT/US2013/067957, having an international filing date of Nov. 1, 2013, which claims the benefit of U.S. Provisional Application No. 61/721,174, filed Nov. 1, 2012, the content of each of the aforementioned applications is herein incorporated by reference in their entirety.

GOVERNMENT SUPPORT

This invention was made with government support under grant nos. HC095159, HC095169, and HC066075, awarded by the National Institutes of Health. The government has certain rights in the invention.

FIELD OF THE INVENTION

The present invention relates generally to cardiac health. More particularly the present invention relates to determining cardiac function using a strain relaxation index.

BACKGROUND OF THE INVENTION

Heart failure and atrial fibrillation are major health concerns, especially when they are clinical outcomes in older individuals. Diastolic dysfunction is a highly prevalent condition and has been associated with heart failure (HF) and atrial fibrillation (AF) in cross-sectional studies. It has traditionally been thought that the physiological cause of HF and AF is abnormal diastolic deformation of the left ventricle. However, this remains largely unproven.

Circumferential strain and strain rate using CMR tagged images has been shown to accurately and reproducibly quantify deformation of the left ventricle (LV) through diastole. Evaluation of diastolic function using cardiac magnetic resonance (CMR) has not been firmly established in spite of a number of efforts. Early-diastolic strain rate and untwist rate have been used as diastolic parameters, but not as metrics to predict cardiovascular events.

It would therefore be advantageous to provide a method and system to predict cardiovascular events using CMR analysis for deformation of the LV through diastole.

SUMMARY OF THE INVENTION

The foregoing needs are met, to a great extent, by the present invention, wherein in one aspect a method for determining cardiac function and health for a subject is provided. The method includes a step of obtaining a cardiac image of the subject using an imaging modality and a step of determining from the cardiac image of the subject systolic, post-systolic, and early diastolic strain peaks. Additionally, the method includes a step of computing a strain rate index (SRI) value using the systolic, post-systolic, and early diastolic strain peaks. The method also includes a step of determining a level of risk of cardiac failure using the SRI value.

In accordance with another aspect of the present invention, the method can include using mid-wall ventricular circumferential strain and strain rates throughout a cardiac cycle of the subject in order to determine the systolic, post-systolic, and early diastolic strain peaks. A treatment plan can be determined for the subject based on the level of risk of cardiac failure. Another step can include assessing cardiac deformation that precedes filling. Varying heart rates can be normalized by applying the difference between a cardiac RR interval and a time to peak systolic strain. The SRI algorithm used can be expressed as $$SRI = \frac{\{(T_{pos} - T_{sys})/(RR\ \text{Interval} - T_{sys})\}}{E_{Ecc}}.$$

The imaging modality can take the form of a magnetic resonance imaging machine, an echocardiography device, or any other suitable device or modality. The method can be used for determining a risk of heart failure and also a risk of atrial fibrillation. It should also be noted that a non-transitory computer readable medium can be programmed to execute the steps of the method. However, any suitable means for executing the method known to or conceivable by one of skill in the art can also be used.

In accordance with another aspect of the present invention, a system for determining cardiac function and health of a subject includes an imaging modality configured to obtain a cardiac image of the subject. The system also includes a processor configured to communicate with the imaging modality and process the cardiac image obtained by the imaging modality. The processor is configured to execute steps including determining from the cardiac image of the subject systolic, post-systolic, and early diastolic strain peaks. The processor is also configured to compute a strain rate index (SRI) value using the systolic, post-systolic, and early diastolic strain peaks. Further, the processor is configured to determine a level of risk of cardiac failure using the SRI value.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

Figure 1:
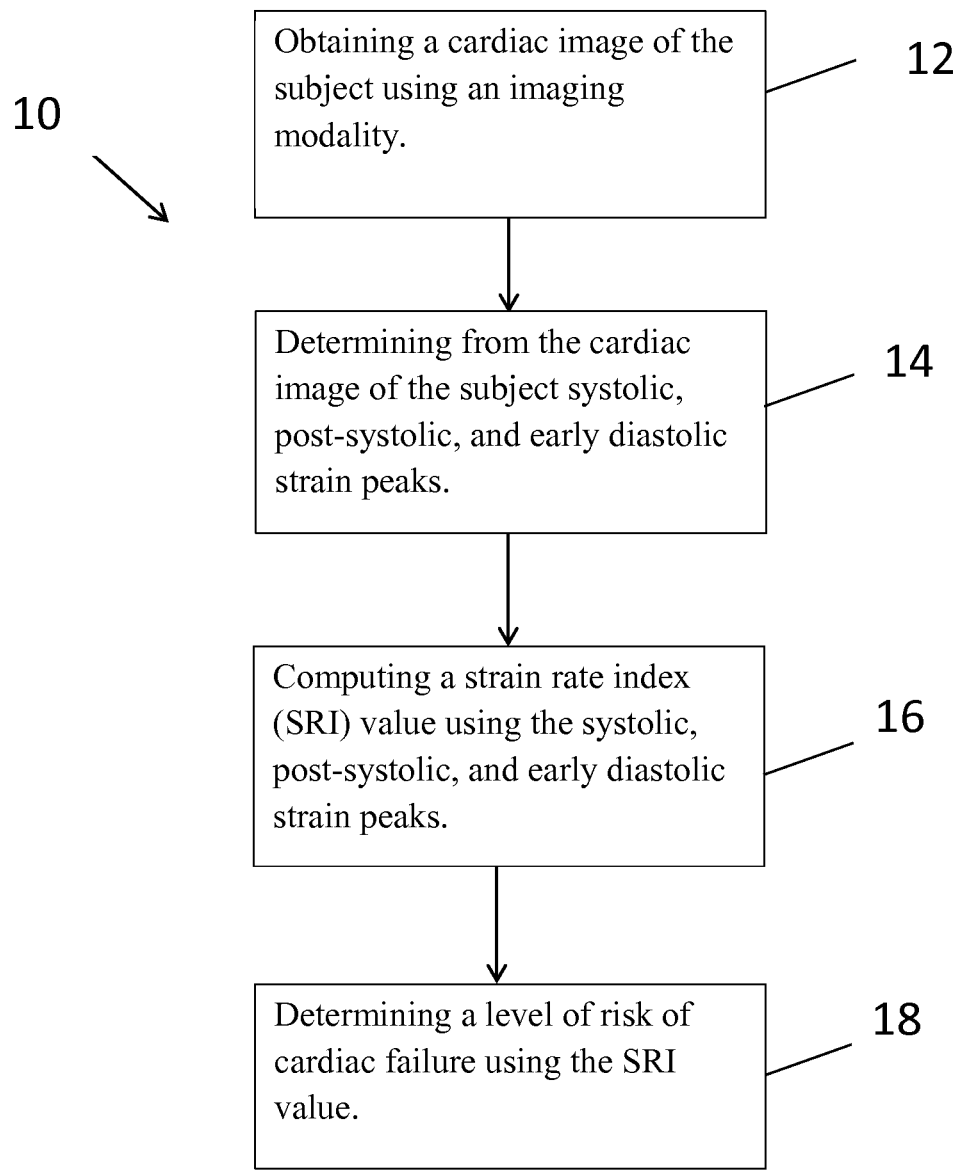
FIG. 1 illustrates a flow diagram of a method to determine cardiac health according to an embodiment of the present invention.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a system and method for determining cardiac events. The system and method include using an imaging modality to obtain a cardiac image of the subject. The image is then used to determine the subject's systolic, post-systolic, and early diastolic strain peaks. Additionally, a strain rate index (SRI) value is computed for the subject using the systolic, post-systolic, and early diastolic strain peaks. The SRI value can then be used to determine a level of risk of cardiac failure. Further, a likelihood of atrial fibrillation can also be determined. The SRI value and risk of cardiac event can then be used to create a treatment plan for the subject, if necessary.

Although LV diastolic dysfunction is an important component of cardiac disease, the power of diastolic function parameters to early predict heart failure (HF) is unknown. The current CMR methods being employed to characterize diastolic function are: peak filling rate, transmitral flow velocity, torsion recoil (untwisting), and early diastolic strain rate. However, the methods used to assess diastolic function by CMR are not firmly established. CMR tagged images can be used to accurately assess LV strain and strain rate curves, reflecting the cardiac deformation. During the cardiac cycle, the circumferential strain reaches a minimum value (maximal shortening) at the end systole, indicated as the peak systolic strain. In sequence, starts the left ventricular relaxation, with the closure of the aortic valve (AVC).

The isovolumic relaxation time (IVRT) is defined as the time between aortic valve closure and mitral valve opening. During IVRT, a positive peak can be observed in the strain rate curve (following the aortic valve closure) and another minimum peak can be seen in the strain curve, the post-systolic strain peak. After the mitral valve opening, another positive peak is presented in the strain rate curve, indicating relaxation in the early diastolic filling phase. The bigger the difference between time to systolic and post-systolic strain peaks in the very early stage of cardiac relaxation, the longer it takes to achieve pressure dropin LV. The drop in LV pressure is related to diastolic filling. This is similar to the IVRT, which increases in the case of diastolic dysfunction; the longer the IVRT, the lower the ability to create early diastolic suction in the LV. The early diastolic strain rate (E peak) decreases with diastolic dysfunction, indicating slower rates of tissue relaxation. The combination of very early relaxation and tissue relaxation properties could be an accurate indicator of diastolic LV function.

SRI should be able to both discriminate heart failure conditions and predict HF over and above traditional risk assessments. It should also compare well with diastolic parameters from echocardiography. Also, while the motivation for SRI came out of a need to assess diastolic function from CMR, SRI can be used to evaluate diastolic function from strain curves (longitudinal, circumferential, radial, maximal shortening, maximal thickening) irrespective of the modality as long as there is sufficient temporal resolution. The very early LV relaxation is characterized by the difference in time between post-systolic and systolic peaks (analogous to IVRT) and values directly related to diastolic dysfunction. The tissue properties can be assessed using the early diastolic strain rate peak and it is inversely related to diastolic dysfunction. The strain relaxation index will be calculated as the difference between post-systolic and systolic times of the strain peaks divided by the early diastolic strain rate peak. The time difference will be normalized by the cardiac RR interval during the CMR scans to adjust for varying heart rates.

FIG. 1 illustrates a flow diagram of a method 10 for determining cardiac function and health for a subject. The method includes step 12 of obtaining a cardiac image of the subject using an imaging modality and step 14 of determining from the cardiac image of the subject systolic, post-systolic, and early diastolic strain peaks. Additionally, the method includes a step 16 of computing a strain rate index (SRI) value using the systolic, post-systolic, and early diastolic strain peaks. The method also includes step 18 of determining a level of risk of cardiac failure using the SRI value.

More particularly, and in addition to the steps illustrated in FIG. 1, the method can include using mid-wall ventricular circumferential strain and strain rates throughout a cardiac cycle of the subject in order to determine the systolic, post-systolic, and early diastolic strain peaks. A treatment plan can be determined for the subject based on the level of risk of cardiac failure. Another step can include assessing cardiac deformation that precedes filling. Varying heart rates can be normalized by applying the difference between a cardiac RR interval and a time to peak systolic strain. The SRI algorithm used can be expressed as $$SRI = \frac{\{(T_{pos} - T_{sys})/(RR \text{ Interval} - T_{sys})\}}{E_{Ecc}}.$$

The imaging modality can take the form of a magnetic resonance imaging machine, an echocardiography device, or any other suitable device or modality. The method can be used to determining heart failure and also atrial fibrillation. It should also be noted that a non-transitory computer readable medium can be programmed to execute the steps of the method. However, any suitable means for executing the method known to or conceivable by one of skill in the art can also be used.

Figure 2:
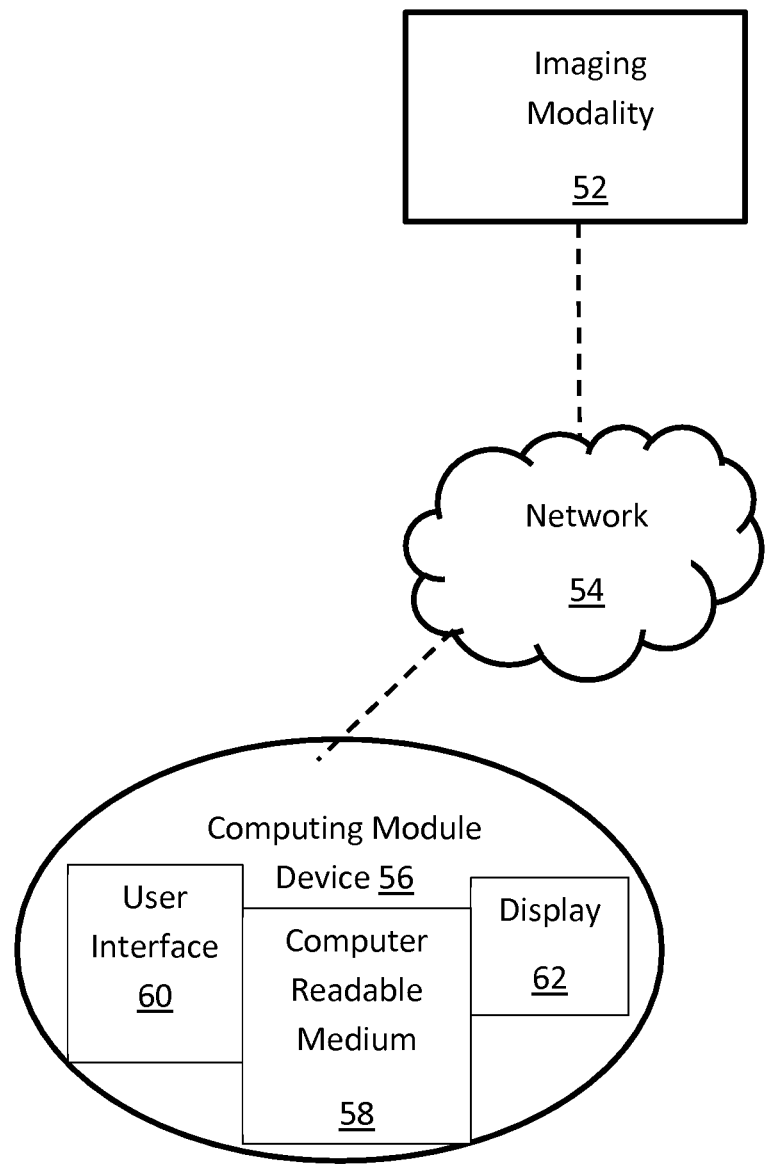
FIG. 2 illustrates a schematic diagram of a system to determine cardiac health according to an embodiment of the present invention.

In order to further illustrate the steps of the method described with respect to FIG. 1, above, FIG. 2 illustrates a schematic diagram of the system 50 used to execute the method. The system 50 includes an imaging modality 52, and it should be noted that, as described above with respect to the method, any suitable imaging modality known to or conceivable by one of skill in the art can be used to obtain images of the subject's heart can be used. Images taken with the imaging modality 52 can be transferred via a network 54, such as a local area network, the internet, a server, or any other suitable networking construct known to or conceivable by one of skill in the art, to a computing device 56. Alternately, the computing device 56 can be a separate device connected to or integrated directly with the imaging modality 52 using a hard wired connection.

Further, with respect to FIG. 2, the computing device 56, preferably, includes a non-transitory computer readable medium 58 or other executable disc known to one of skill in the art. The non-transitory computer readable medium contains code such that the method described herein can be executed and used to determine cardiac function. The non-transitory computer readable medium 58 can also include a user interface 60 and a display 62 such that an operator can interact with the system 50 in order to input any necessary values or configure the functionality of the program as well as view the results of the method executed by the computing device 56. The display can take the form of a computer screen, tablet computing device, smartphone, television, or other display device known to one of skill in the art.

It should be noted that a non-transitory computer readable medium can be programmed to execute the above described method. The non-transitory computer readable medium can be loaded onto a computing device or server. The computing device or server can also be in networked communication with a source of data for analysis by the program loaded onto the non-transitory computer readable medium. The computing device can take any suitable form known to one of skill in the art such as a personal computer, tablet computing device, smartphone, processor, server, etc. The non-transitory computer readable medium can either be loaded directly onto a hard drive of the computing device, can be on a separate hard disk or CD-ROM, can be on the server described above, another independent server, a network, or any other suitable configuration known to or conceivable by one of skill in the art. A non-transitory computer readable medium is defined as any article of manufacture that contains data that can be read by a computer. Such computer readable media includes but is not limited to magnetic media, such as a floppy disk, a flexible disk, a hard disk, reel-to-reel tape, cartridge tape, cassette tape or cards; optical media such as CD-ROM and writeable compact disc; magneto-optical media in disc, tape or card form; and paper media, such as punched cards and paper tape. The non-transitory computer readable medium contains code such that the method described herein can be executed.

Figure 3:
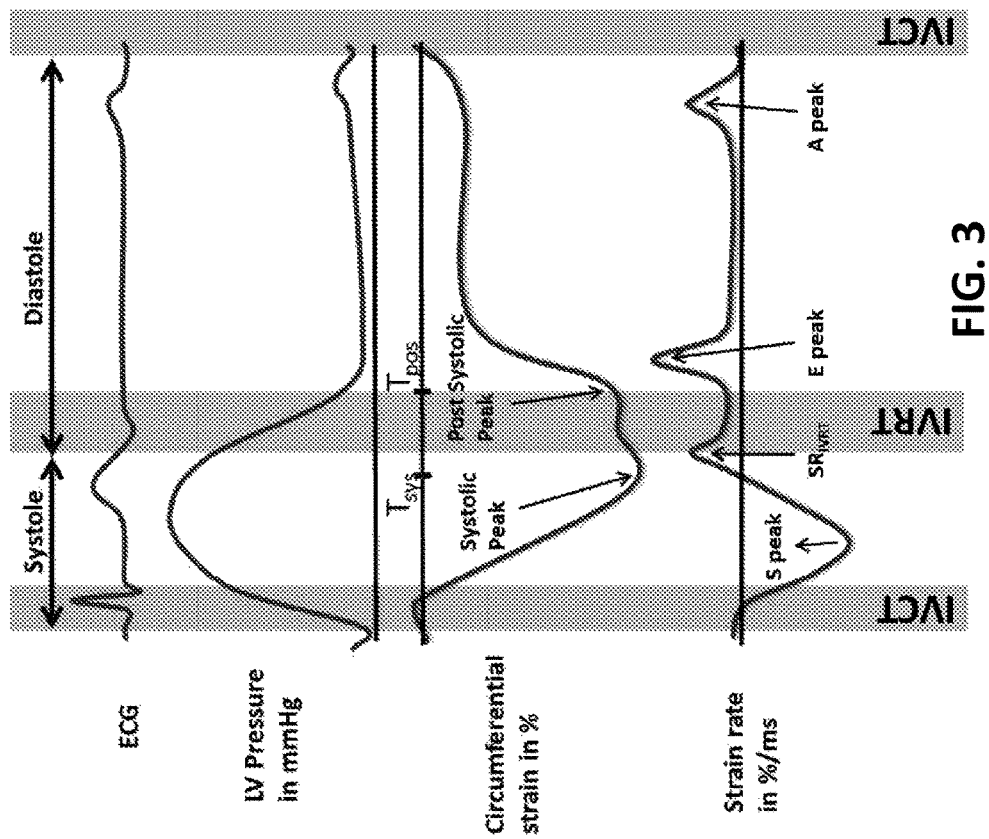
FIG. 3 illustrates the calculation of the proposed SRI from the circumferential strain (top) and strain rate curves (bottom). More negative strain values indicate greater circumferential shortening. SRI is calculated as the ratio of the duration of very early relaxation to the duration of the diastolic interval, divided by the early-diastolic strain rate peak.

FIG. 3 illustrates deformation curves through the cardiac cycle. During the cardiac cycle, the circumferential strain reaches a minimum value (maximal shortening) at the peak systolic strain. In sequence, starts the left ventricular relaxation, followed by the closure of the aortic valve (AVC). During the isovolumic relaxation time (IVRT), a positive peak can be observed in the strain rate curve following the aortic valve closure. In sequence, the post-systolic strain peak can be seen. The strain rate curve also shows a positive peak after the mitral valve opening, indicating relaxation.

The bigger the difference between time to systolic and post-systolic strain peaks in the early stage of cardiac relaxation, the longer it takes to achieve the pressure drop required for diastolic filling. This is similar to the IVRT, which increases in the case of diastolic dysfunction. Moreover, the early diastolic strain rate (E peak) decreases with diastolic dysfunction, indicating stiffer tissue. Therefore, the combination of early cardiac relaxation and tissue relaxation properties is proposed as an accurate indicator of diastolic LV function. As noted above, SRI can be calculated as follows:

$$SRI = \frac{\{(T_{pos} - T_{sys})/(RR \text{ Interval} - T_{sys})\}}{E_{Ecc}}$$

As calculated in the algorithm above, SRI is the difference between post-systolic ($T_{pos}$) and systolic ($T_{sys}$) times of the strain peaks divided by the early diastolic strain rate ($E_{Ecc}$) peak. The time difference was normalized by the difference between the cardiac RR interval and the time to peak systolic strain, representing the total interval of relaxation.

Example

The following example is included merely as an illustration of the present method and is not intended to be considered limiting. This example is one of many possible applications of the methods described above. Any other suitable application of the above described methods known to or conceivable by one of skill in the art could also be created and used. While this example is directed to analysis of early diastolic function with a CMR image, any suitable point in the cardiac cycle can be studied with any suitable imaging modality, known to or conceivable by one of skill in the art.

The study was performed using data from the multi-ethnic study of atherosclerosis (MESA) is a prospective, population-based observational cohort study of 6814 men and women representing four racial/ethnic groups (Caucasian, African-American, Hispanic and Chinese-American), aged 45-84 years and free of clinical cardiovascular disease at enrolment. As part of the baseline examination, between 2001 and 2002, a total of 5004 (73%) participants received comprehensive cardiac MRI studies at six field centers. The institutional review boards of all MESA field centers approved the study protocol. Of the 5004 individuals who underwent cardiac MRI examination, 1617 participants with available clinical covariate data agreed to a slightly longer examination to accommodate MRI tagging analyses. Of these participants, deformation data could not be analyzed owing to data acquisition failure or of insufficient quality for strain and strain rate determination in 73 participants. The remaining 1544 participants with complete circumferential strain, strain rate and strain relaxation rate measurements were included in this analysis. Of these 1544 participants, 743 underwent a follow-up examination after an 8-year period, with MRI tagging as a part of the imaging protocol. Of these, 27 were excluded because of insufficient quality of determined strain or data acquisition failure. Tagged MR protocol and analysis methods remained the same in the baseline and follow-up visits.

Images were acquired in whole body scanners using electrocardiogram triggered segmented k-space fast spoiled gradient-echo pulse sequences during breath holds. CMR myocardial horizontal and vertical tagging was performed on three LV short-axis slices (base, mid, apex) by non-selective radiofrequency pulses separated by a spatial modulation of magnetization (SPAMM) encoding gradients. CMR myocardial horizontal and vertical tagging was performed on three LV short-axis slices (base, mid, apex) by non-selective radiofrequency pulses separated by a spatial modulation of magnetization (SPAMM) encoding gradients. Parameters for tagged images were: field of view, 40 cm; slice thickness 7 to 8 mm; repetition time, 6 ms; echo time, 3 ms; flip angle, 10° to 12°; phase encoding views, 128 with 6 phase encoding views per segment; temporal resolution, 40 ms; tag spacing, 7 mm. All MRI studies were submitted to the major MRI reading center of the MESA trial located in Johns Hopkins Hospital. The analyses of all acquired images were performed in the core laboratory of the MRI reading center.

Short-axis tagged slices were analyzed by the harmonic phase method. Systolic and post-systolic circumferential strain peaks were assessed from the mid-wall, mid-ventricular circumferential strain (Ecc) and strain rates through the cardiac cycle. These were then used to compute SRI. Ecc values are conventionally negative to express circumferential shortening.

With respect to risk factors, serum concentration of NT-proBNP was measured using a highly sensitive and specific immunoassay based on a double-antibody sandwich technique (Roche Diagnostics Corporation, Indianapolis, Ind.). Coronary calcium scores were obtained from the phantom-adjusted mean Agatston calcium score.

A telephone interviewer contacted each participant (or representative) every 6 to 9 months to inquire about all interim hospital admissions, cardiovascular outpatient diagnoses, and deaths. Two physicians reviewed all records for independent end point classification and assignment of event dates.

Criteria for HF as an end-point included symptomatic HF diagnosed by a physician and patient receiving medical treatment for HF and 1) pulmonary edema/congestion by chest X-ray, and/or 2) dilated ventricle or poor LV function by echocardiography or ventriculography, or evidence of LV diastolic dysfunction. Participants who had a physician's diagnosis of HF were classified as having HF. Criteria for AF as end-point was if AF was diagnosed present on an ECG obtained as part of the study procedure. The combined end-point was ascertained as the first-documented event of either HF or AF.

All continuous variables were visually inspected for normality of distribution. Continuous presented as mean/SD, and categorical presented as %. SRI, early diastolic strain rate and NT-proBNP showed skewed distributions and underwent natural logarithmic transformation. Longitudinal differences in SRI were assessed with a Student's T-test in the population with a follow-up MRI exam.

Univariate analysis using Cox regression was used to assess the performance of SRI and peak early diastolic circumferential strain to predict the combined end-point. The AHA recommendations for evaluations of novel markers of cardiovascular risk was used as the basis of statistical analysis. Cox proportional hazards models were also used to assess the association of SRI to events independent of conventional risk factors (age, race, gender; body mass index, smoking status, systolic blood pressure, diastolic blood pressure, use of hypertension medication, diabetes mellitus/impaired fasting glucose, LDL cholesterol, total cholesterol). The hazard ratio, associated confidence intervals and p-value were used to evaluate this association. The Schoenfeld's test was used to confirm proportionality of the hazards assumption. Harrell's C-statistic was used to measure the area under the receiver-operator curves to measure the predictive discrimination of multi-markers for each end-point. The added value of SRI to the existing model was calculated from the difference in the calculated c-statistic and the significance of this difference.

Integrated discrimination index (IDI) was calculated to report the improvement in discrimination based on the survival probabilities with the addition of SRI to the conventional risk factors. Net reclassification index (NRI) was used to quantify the number of individuals correctly and incorrectly reclassified with the addition of the new biomarker in to low, intermediate and high risk categories. Risk categories of <5%, 5-20% and >20% were used in the measurement of NRI for HF and the combined end-points. For AF as the end-point, categories were defined as <5%, 5-15% and >15%.

A secondary analysis was performed to test the ability of SRI to predict HF and/or AF independent of other established risk factors in addition to the conventional risk factors. Due to lack of availability of all covariates, this was done in a reduced population. Cox proportional hazards models were also used to assess the association of SRI to events independent of conventional and established risk factors. Models considered were those with the progressive addition of established risk factors to conventional risk actors—coronary calcium score (model 1), NT-proBNP (model 2), LV mass index (model 3) and LV ejection fraction (model 4).

Calibration of the models was confirmed using the Gronnesby-Borgan tests to compare the expected and observed event rates across deciles for each model, See Table 9. Kaplan-Meier curves of event incidence were used for comparison of survival rates across tertiles of SRI. Two tailed p-values were <0.05 used for significance testing. All statistical analysis was done using STATA v11.0 (StataCorp LP, CollegeStation, Tex., USA).

Figure 4:
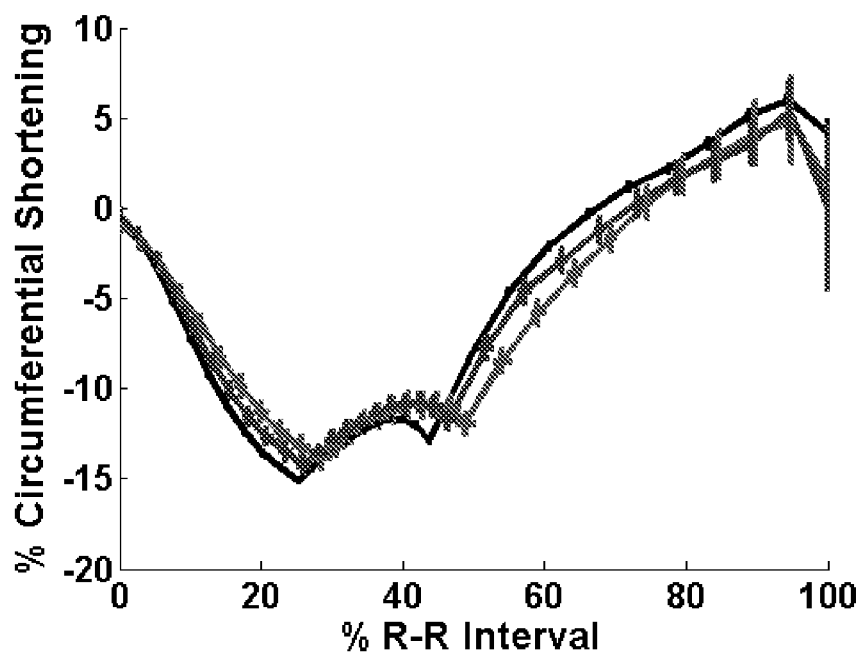
FIG. 4 illustrates average curves of circumferential strain over time normalized to the R-R interval in all studies, participants with HF and participants with AF. The error bars indicate the standard error in both the time (x-axis) and % strain (y-axis). This plot shows that in HF and AF, there is reduced shortening and impaired early cardiac relaxation. The average interval between the systolic and post-systolic peaks was increased in HF (190.5 ms, p=0.17) and AF (197.4 ms, p<0.05) compared to that in those without events (172.3 ms). This increase was significant (p<0.05) after normalization by the total relaxation interval (HF=28.9%, AF=27.8%, without events=24.8%).

Baseline characteristics of the participants are provided in Table 1. HF was incident in 2.6% of the population while AF was incident in 3.9% over the 8-year follow-up period. 14 participants had both AF and HF, 12 of those with AF preceding HF. Incidences of HF and AF were associated with increased age, male gender, higher BMI, higher systolic blood pressure, higher levels of coronary calcium, higher levels of NT-proBNP, decreased early-diastolic strain rate and increased SRI. FIG. 4 illustrates that the normalized relaxation interval increases in participants with HF or AF compared to those without.

In the longitudinal follow-up, log SRI increased (baseline=0.74±0.58, follow-up=1±0.58, p<0.05) and early diastolic strain rate decreased (baseline=0.12±0.06, follow-up=0.10±0.04, p<0.05) in the population (n=696) without events. There were only twenty individuals as part of the follow-up MRI exams with HF/AF and hence SRI between the visits was not compared.

Figure 5:
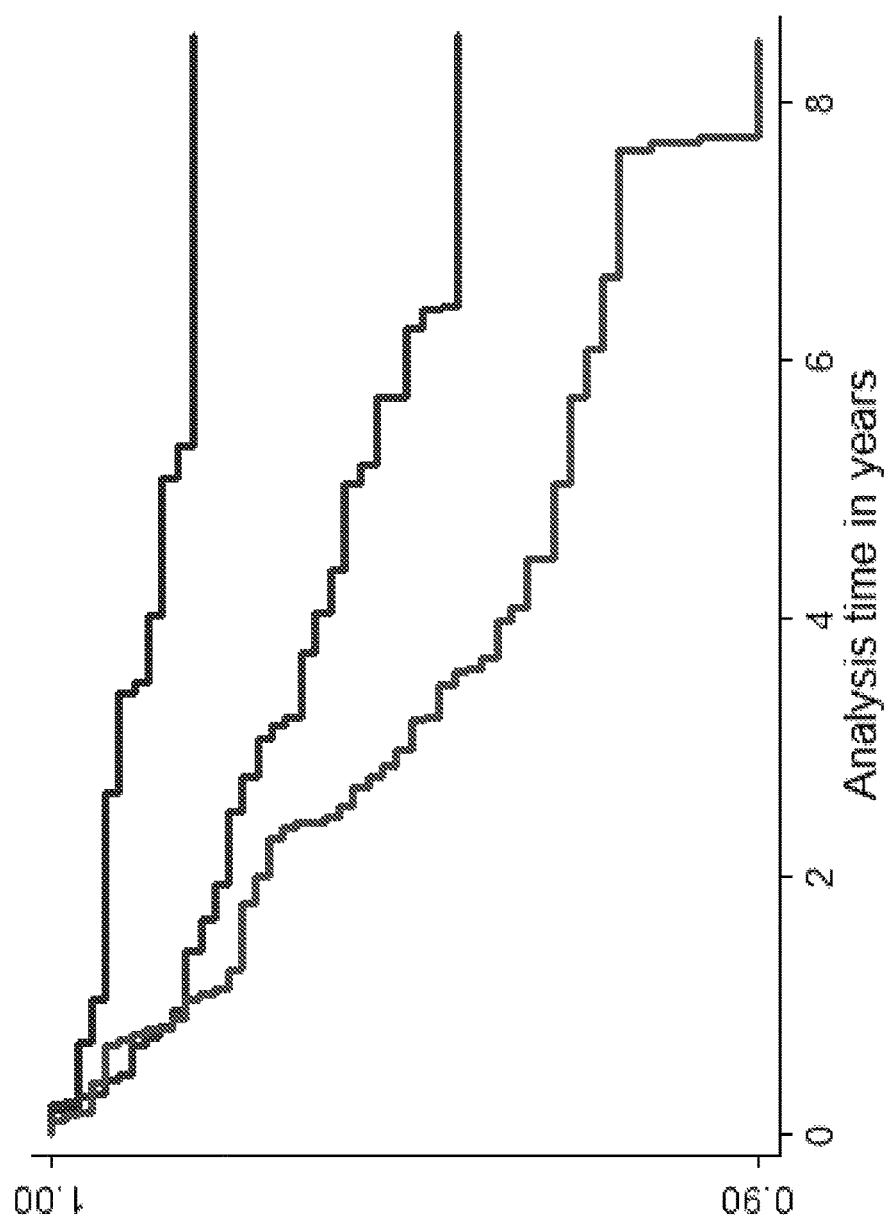
FIG. 5 illustrates the Kaplan-Meier survival curves for combined end-points across tertiles of log (SRI). Individuals were free of AF or HF at baseline. log (SRI) expressed as median (minimum, maximum) across three tertiles was Q1: 0.119 (−0.2.239, 0.544), Q2: 0.805 (0.544, 1.034), Q3: 1.378 (1.034, 3.471).

FIG. 5 illustrates the Kaplan-Meier survival curves for the combined end-point across tertiles of SRI. Univariate and multivariate analyses of early-diastolic strain rate and SRI are shown in Table 2 for the combined end-point. The hazard ratio (HR) for SRI and the early diastolic strain rate were both significant for the combined end-point for the univariate analysis and after adjustment for conventional risk factors. The C-statistic for prediction of combined endpoints was greater for SRI compared to the early diastolic strain rate. Table 3 provides analysis with HF and AF as end-points.

For the combined end-point, there was a significant improvement in discrimination (IDI) with the addition of SRI to the conventional risk factors of 1.2% (p<0.05). The IDI for HF and AF as end-points were 1.5% (p=0.07) and 0.9% (p<0.05) respectively.

Risk category reclassification (NRI) was higher for prediction of combined end-points as compared to only the conventional risk factors. The improvement in the net reclassification was both a result of upward reclassification of events to higher risk categories and a downward reclassification of non-events (see Table 4). The NRI for HF and AF were 14.4% (p=0.05) and 5.9% (p–0.14) respectively (see Table 5).

A secondary analysis was performed in a reduced population (see Table 6). In this analysis (see Table 4), the HR for SRI was stable and significant for the combined end-point across all models tested after adjustments for established risk factors (categories of calcium score, NT-proBNP, LV mass index and LV ejection fraction). The area under the receiver-operator curve improved with the addition of SRI for all the models. A similar table for analysis with HF and AF as end-points (see Table 7).

Gronnesby-Borgan calibration tests were used to compare the expected and observed event rates across deciles for each model (see Table 8), without significant difference (all p>0.05).

SRI increases compared to the baseline after an 8-year follow-up exam in the same population (excluding those with HF/AF) indicating that diastolic dysfunction increases with age. The AHA-recommended guidelines were used to establish SRI as a new biomarker, and a powerful predictor of HF and/or AF, after a 8-year follow-up period, independent of conventional and established risk factors. Univariate analysis showed that SRI was better than tagged MRI-derived peak early diastolic strain rate, an index of tissue stiffness as a predictor of the combined end-point. Multivariate analysis revealed that SRI was an independent predictor of HF or AF after adjustment for conventional and established risk factors. Moreover, adding SRI to conventional risk factors significantly improved discrimination and reclassification for the combined clinical outcome of HF and AF in a large asymptomatic population.

Post-systolic shortening has mainly been used in the study of ischemic segments, but it also can be found in healthy hearts. While the term "post-systolic shortening" has generally been used only when the post-systolic strain is greater than the systolic strain, we use it to denote the local minimum found on the strain curve prior to the time of peak early-diastolic strain rate irrespective of whether it was greater than the peak systolic strain. The interval between the occurrence of the post-systolic peak and the peak systolic strain is a measure of cardiac relaxation and is influenced by LV filling pressures, it is clearly increased in those with HF and AF compared to those without events, as illustrated in FIG. 4. IVRT from tissue Doppler imaging has been shown to be a load independent measure of active relaxation. SRI also accounts for ventricular stiffness measure by early-diastolic strain rate (another load independent quantity), influenced by fibrosis, myocyte loss and changes in LV geometry. The combination of the two improves the predictive ability of SRI over the conventionally used early-diastolic strain rate. To our knowledge, this is the first CMR-derived measurement of diastolic function that predicts the combined end-point.

In this example, SRI is calculated from mid-wall, mid-ventricular circumferential strain from a single tagged MR slice. While tagged MRI has been the gold standard for strain imaging, in theory, SRI could also be calculated speckle tracking echocardiography (STE). SRI can also potentially be calculated from longitudinal strain and radial strain curves. Therefore, SRI could be a very useful measurement for evaluating diastolic function in clinical practice.

It should be noted that although the invention is described with respect to studying early diastolic deformation it is possible that this analysis could be applied to different stages of the cardiac cycle. It should also be noted that imaging modalities other than a CMR could potentially be used to execute the present method. Of course, it is also possible that an imaging modality currently in development or an imaging modality yet to be conceived could also be used to implement this invention.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

TABLE 1

Baseline Characteristics

| Variable | Mean (SD) | | | |
| --- | --- | --- | --- | --- |
|  | Overall (n = 1544) | HF (n = 36) | AF (n = 57) | Combined (n = 80) |
| Age (y) | 65 ± 9.7 | 70.2 ± 8.2 | 70.7 ± 9.1 | 70.3 ± 8.7 |
| Body Mass Index (kg/m$^2$) | 27.8 ± 4.7 | 28.9 ± 4.1 | 28.3 ± 4.1 | 28.6 ± 4.3 |
| Sys. blood pressure (mmHg) | 128 ± 20.7 | 134.8 ± 20.0 | 139.1 ± 22.5 | 136.9 ± 22.3 |
| Diast. blood pressure (mmHg) | 71.8 ± 10.1 | 70.4 ± 13.1 | 73.1 ± 11.8 | 72.2 ± 12.1 |
| Heart rate (bpm) | 62.3 ± 9.5 | 62.2 ± 9.1 | 59.5 ± 9.9 | 60.3 ± 9.9 |
| HDL cholesterol (mg/dl) | 50.6 ± 14.5 | 49.1 ± 12.1 | 49 ± 14.1 | 48.8 ± 13.8 |

TABLE 1-continued

Baseline Characteristics

| | | | | |
|---|---|---|---|---|
| Total cholesterol (mg/dl) | 194.2 ± 34.9 | 180.8 ± 26.9 | 183.9 ± 30.1 | 181.5 ± 28.8 |
| Ecc E Peak (%/ms) | 0.12 ± 0.06 | 0.10 ± 0.05 | 0.10 ± 0.05 | 0.10 ± 0.05 |
| log(SRI) (ms/%) | 0.78 ± 0.56 | 1.12 ± 0.45 | 1.01 ± 0.52 | 1.04 ± 0.51 |

| | Proportion of Participants (%) | | | |
|---|---|---|---|---|
| Variable | Overall (n = 1544) | HF (n = 36) | AF (n = 57) | Combined (n = 80) |
| Men | 53 | 72.9 | 69.5 | 71.2 |
| Race | | | | |
| Caucasian | 28.9 | 16.3 | 47.5 | 34.3 |
| Chinese-American | 14.6 | 10.8 | 11.9 | 10.9 |
| African-American | 27.8 | 27 | 16.9 | 21.9 |
| Hispanic | 28.7 | 45.9 | 23.7 | 32.9 |
| Smokers | | | | |
| Former | 35.9 | 50 | 36.2 | 40.7 |
| Current | 11.3 | 11.1 | 12.1 | 11.1 |
| Diabetes/Impaired Fasting glucose | 31.2 | 54 | 35.6 | 63 |
| Use of hypertension medication | 39.9 | 54.1 | 57.6 | 58.5 |

Shown are baseline characteristics of individuals who underwent tagged MRI at baseline and with information on conventional risk factors For continuous variables, mean ± SD are given and for categorical variables, n (%) are given.

TABLE 2

Prediction and discrimination assessment on the combined endpoint of HF and/or AF for CMR-derived diastolic parameters (n = 1544, n = 80)

| Diastolic parameter | HR (95% CI) | | Discrimination | | |
|---|---|---|---|---|---|
| | Univariate | Multivariate | AUC | Diff | P |
| log(Ecc E Peak) | 0.32 (0.19, 0.53) | 0.50 (0.30, 0.83) | 0.767 | 0.005 | 0.520 |
| log(SRI) | 2.54 (1.76, 3.66) | 1.90 (1.30, 2.77) | 0.779 | 0.018 | 0.056 |

Endpoint is participants that had atrial fibrillation and heart failure, whichever happened first. In multivariate analysis, adjustments were made for age, race, gender; body mass index, smoking status, systolic blood pressure, diastolic blood pressure, use of hypertension medication, diabetes mellitus/impaired fasting glucose, LDL cholesterol, total cholesterol, log (SRI).

TABLE 3

Risk Category Reclassification Using log (SRI) for combined endpoint of AF or HF (n = 1544).

| Conventional Risk Factors | Conventional risk factors + log (SRI) | | | |
|---|---|---|---|---|
| | <5% | 5%-20% | >20% | Total |
| Non-Events | | | | |
| <5% | 845 | 46 | | 891 |
| 5%-20% | 83 | 425 | 18 | 526 |
| >20% | | 8 | 39 | 47 |
| Total | 928 | 479 | 57 | 1464 |
| Events | | | | |
| <5% | 17 | 2 | | 19 |
| 5%-20% | 1 | 46 | 3 | 50 |
| >20% | | | 11 | 11 |
| Total | 18 | 48 | 14 | 80 |

Net reclassification index (NRI) with the addition of log(SRI). Conventional risk factors included age, race, gender; body mass index, smoking status, systolic blood pressure, diastolic blood pressure, use of hypertension medication, diabetes mellitus/impaired fasting glucose, LDL cholesterol, total cholesterol. NRI for combined end-point = 0.068(p = 0.03).

TABLE 4

Prediction and discrimination assessment on the combined endpoint of HF and/or AF for CMR-derived diastolic parameters (n = 1255, 65 events)

| | HR (95% CI) | AUC | Diff | P |
|---|---|---|---|---|
| Model 1 | 1.78 (1.14, 2.78) | 0.793 | 0.012 | 0.129 |
| Model 2 | 1.79 (1.13, 2.85) | 0.823 | 0.008 | 0.291 |
| Model 3 | 1.77 (1.11, 2.82) | 0.825 | 0.006 | 0.435 |
| Model 4 | 1.79 (1.12, 2.85) | 0.827 | 0.006 | 0.400 |

Endpoint is participants that had atrial fibrillation or heart failure combined. In multivariate analysis, adjustments to different variables were made for each model. Model 1: age, race, gender; body mass index, smoking status, systolic blood pressure, diastolic blood pressure, use of hypertension medication, diabetes mellitus/impaired fasting glucose, LDL cholesterol, total cholesterol, categories of coronary calcium, log (SRI); Model 2: Model 1 + log(BNP); Model 3: Model 2 + LV mass index; Model 4: Model 3 + LV ejection fraction.

TABLE 5

Prediction and discrimination assessment on the endpoint of HF and AF for CMR-derived diastolic parameters (n = 1544).

| Diastolic parameter | HR (95% CI) | | Discrimination | | |
|---|---|---|---|---|---|
| | Univariate | Multivariate | AUC | Diff | P |
| HF (n = 36) | | | | | |
| log(Ecc E Peak) | 0.26 (0.12, 0.55) | 0.43 (0.20, 0.93) | 0.790 | 0.011 | 0.419 |
| log(SRI) | 3.22 (1.91, 5.43) | 2.33 (1.35, 4.02) | 0.810 | 0.031 | 0.033 |

TABLE 5-continued

Prediction and discrimination assessment on the endpoint of HF and AF for CMR-derived diastolic parameters (n = 1544).

| Diastolic parameter | HR (95% CI) Univariate | HR (95% CI) Multivariate | Discrimination AUC | Diff | P |
|---|---|---|---|---|---|
| AF (n = 57) | | | | | |
| Ecc E Peak | 0.39 (0.22, 0.69) | 0.57 (0.32, 1.01) | 0.777 | 0.004 | 0.601 |
| log(SRI) | 2.35 (1.52, 3.62) | 1.79 (1.14, 2.79) | 0.782 | 0.009 | 0.403 |

Endpoint is participants that had atrial fibrillation and heart failure, whichever happened first. In multivariate analysis, adjustments were made for age, race, gender; body mass index, smoking status, systolic blood pressure, diastolic blood pressure, use of hypertension medication, diabetes mellitus/impaired fasting glucose, LDL cholesterol, total cholesterol, log (SRI).

TABLE 6

Risk Category Reclassification Using log (SRI) for endpoints of AF and HF (n = 1544).

| Conventional Risk Factors | Conventional risk factors + log (SRI) | | | |
|---|---|---|---|---|
| HEART FAILURE | <5% | 5%-20% | >20% | Total |
| Non-Events | | | | |
| <5% | 1225 | 58 | | 1283 |
| 5%-20% | 73 | 127 | 13 | 213 |
| >20% | | 5 | 7 | 12 |
| Total | 1298 | 190 | 20 | 1508 |
| Events | | | | |
| <5% | 13 | 5 | | 18 |
| 5%-20% | 1 | 12 | 1 | 14 |
| >20% | | | 4 | 4 |
| Total | 14 | 17 | 5 | 36 |
| ATRIAL FIBRILLATION | <5% | 5%-15% | >15% | Total |
| Non-Events | | | | |
| <5% | 1089 | 42 | | 1129 |
| 5%-15% | 56 | 240 | 15 | 313 |
| >15% | | 11 | 34 | 45 |
| Total | 1145 | 293 | 49 | 1487 |
| Events | | | | |
| <5% | 19 | 2 | | 21 |
| 5%-15% | 1 | 26 | 2 | 29 |
| >15% | | 1 | 6 | 7 |
| Total | 20 | 29 | 8 | 57 |

Net reclassification index (NRI) with the addition of log(SRI). Conventional risk factors included age, race, gender; body mass index, smoking status, systolic blood pressure, diastolic blood pressure, use of hypertension medication, diabetes mellitus/impaired fasting glucose, LDL cholesterol, total cholesterol. NRI for HF = 0.144(p = 0.05) and AF = 0.059(p = 0.14)

TABLE 7

Baseline Characteristics

| | Mean (SD) | | | |
|---|---|---|---|---|
| Variable | Overall (n = 1255) | HF (n = 28) | AF (n = 49) | Combined (n = 65) |
| Age (y) | 65.3 ± 9.6 | 71.1 ± 7.5 | 70.9 ± 9.4 | 70.7 ± 8.6 |
| Body Mass Index (kg/m$^2$) | 27.6 ± 4.7 | 29.0 ± 4.2 | 28.1 ± 4.2 | 28.4 ± 4.3 |
| Sys. blood pressure (mmHg) | 128.2 ± 20.7 | 134.9 ± 19.8 | 140.4 ± 21.5 | 138.2 ± 21.6 |
| Diast. blood pressure (mmHg) | 71.9 ± 10.1 | 70.2 ± 14 | 73.6 ± 11.9 | 72.3 ± 12.5 |
| Heart rate (bpm) | 62.4 ± 9.6 | 63.3 ± 9.3 | 60.6 ± 9.7 | 61.2 ± 9.9 |
| HDL cholesterol (mg/dl) | 50.6 ± 14.6 | 49.7 ± 12.7 | 49.8 ± 14.6 | 49.7 ± 14.3 |
| Total cholesterol (mg/dl) | 194 ± 34.9 | 181 ± 27.6 | 186.6 ± 30 | 183.9 ± 29.2 |
| log(BNP) (pg/ml) | 4 ± 1.19 | 5.51 ± 1.39 | 5.13 ± 1.29 | 5.14 ± 1.34 |
| LV mass index (g/m$^{1.7}$) | 61.3 ± 14.2 | 76.4 ± 21.4 | 69.5 ± 19.5 | 70.2 ± 18.6 |
| LV EF (%) | 69 ± 7.6 | 63.7 ± 11.6 | 67.9 ± 10.9 | 67.3 ± 10.6 |
| Ecc E Peak (%/ms) | 0.12 ± 0.06 | 0.10 ± 0.04 | 0.10 ± 0.04 | 0.10 ± 0.04 |
| log(SRI) (ms/%) | 0.76 ± 0.60 | 1.07 ± 0.42 | 1.01 ± 0.52 | 1.00 ± 0.49 |

| | Proportion of Participants (%) | | | |
|---|---|---|---|---|
| Variable | Overall (n = 1255) | HF (n = 28) | AF (n = 49) | Combined (n = 65) |
| Men | 54.5 | 71.4 | 71.4 | 70.7 |
| Race | | | | |
| Caucasian | 29.9 | 17.9 | 51.1 | 38.5 |
| Chinese-American | 16.2 | 10.7 | 10.2 | 10.8 |
| African-American | 23.9 | 21.4 | 14.2 | 16.9 |
| Hispanic | 30 | 50 | 24.5 | 33.8 |
| Smokers | | | | |
| Former | 36.5 | 51.9 | 37.5 | 42.2 |
| Current | 10.8 | 11.1 | 12.5 | 10.9 |
| Diabetes/Impaired Fasting glucose | 31.9 | 60.7 | 36.7 | 46.2 |
| Use of hypertension medication | 39.5 | 50 | 55.1 | 55.4 |

TABLE 7-continued

Baseline Characteristics

|  | Mean (SD) | | | |
| --- | --- | --- | --- | --- |
| Calcium Score Categories | | | | |
| 0 | 44.2 | 17.8 | 16.4 | 20.1 |
| 1-100 | 27.6 | 25 | 28.6 | 27.6 |
| 101-300 | 14.1 | 14.3 | 16.3 | 15.4 |
| >300 | 14.1 | 42.9 | 48.7 | 36.9 |

Shown are baseline characteristics of individuals who underwent tagged MRI at baseline and with information on conventional risk factors. For continuous variables, mean ± SD are given and for categorical variables, n (%) are given.

TABLE 8

Prediction and discrimination assessment on the endpoint of HF and AF for CMR-derived diastolic parameters (n = 1255)

|  | HR (95% CI) | AUC | Diff | P |
| --- | --- | --- | --- | --- |
| HF (n = 28) | | | | |
| Model 1 | 2.34 (1.17, 4.71) | 0.827 | 0.030 | 0.025 |
| Model 2 | 2.34 (1.11, 4.94) | 0.898 | 0.019 | 0.094 |
| Model 3 | 2.20 (1.04, 4.67) | 0.904 | 0.012 | 0.221 |
| Model 4 | 2.31 (1.08, 4.96) | 0.910 | 0.011 | 0.273 |
| AF (n = 49) | | | | |
| Model 1 | 1.85 (1.10, 3.12) | 0.793 | 0.006 | 0.549 |
| Model 2 | 1.80 (1.04, 3.11) | 0.837 | 0.004 | 0.624 |
| Model 3 | 1.79 (1.03, 3.10) | 0.840 | 0.005 | 0.530 |
| Model 4 | 1.79 (1.03, 3.10) | 0.840 | 0.005 | 0.565 |

Endpoint is participants that had atrial fibrillation and heart failure, whichever happened first. In multivariate analysis, adjustments to different variables were made for each model. Model 1: age, race, gender; body mass index, smoking status, systolic blood pressure, diastolic blood pressure, use of hypertension medication, diabetes mellitus/impaired fasting glucose, LDL cholesterol, total cholesterol, categories of coronary calcium; Model 2: Model 1 + log(BNP); Model 3: Model 2 + LV mass index; Model 4: Model 3 + LV ejection fraction.

TABLE 9

Calibration of Models.

|  | HF | AF | Combined |
| --- | --- | --- | --- |
| CRF | 0.41 | 0.69 | 0.29 |
| Model 1 | 0.14 | 0.47 | 0.27 |
| Model 2 | 0.07 | 0.47 | 0.12 |
| Model 3 | 0.09 | 0.48 | 0.13 |
| Model 4 | 0.37 | 0.70 | 0.12 |

Table shows the p-value for the Gronnesby-Borgan calibration tests for deciles of predicted risk. HF: heart failure. AF: atrial fibrillation. Combined: participants that had atrial fibrillation or heart failure. LR: likelihood-ratio.
In multivariate analysis, adjustments to different variables were made for each model. CRF: age, race, gender, SRI, body mass index, smoking status, systolic blood pressure, diastolic blood pressure, use of hypertension medication, diabetes mellitus/impaired fasting glucose, LDL cholesterol, total cholesterol; Model 1: CRF + categories of coronary calcium; Model 2: Model 1 + log(BNP); Model 3: Model 2 + LV mass index; Model 4: Model 3 + LV ejection fraction.

What is claimed is:

1. A method for determining a treatment plan for a subject based upon determining cardiac function and health for the subject, comprising:
   obtaining, by a device and from an imaging modality, a plurality of cardiac images of the subject;
   determining, by the device and from the plurality of cardiac images of the subject:
      a first time associated with a systolic strain peak,
      a second time associated with a post-systolic strain peak, and
      an early diastolic strain peak;
   computing, by the device, a strain rate index (SRI) value using the first time associated with the systolic strain peak, the second time associated with the post-systolic strain peak, and the early diastolic strain peak,
      the SRI being computed based upon a difference between the first time associated with the systolic strain peak and the second time associated with the post-systolic strain peak divided by the early diastolic strain peak;
   determining, by the device, a level of risk of cardiac failure using the SRI value;
   determining, by the device, the treatment plan for the subject based on the level of risk of cardiac failure; and
   providing, by the device, information associated with the level of risk of cardiac failure and the treatment plan for review by a medical professional.

2. The method of claim 1, further comprising:
   determining the systolic strain peak and the post-systolic strain peak using mid-wall ventricular circumferential strain associated with a cardiac cycle of the subject; and
   determining the early diastolic strain peak using strain rates associated with the cardiac cycle of the subject.

3. The method of claim 1, further comprising:
   calculating a difference between a cardiac RR interval and the first time associated with the systolic strain peak when computing the SRI value.

4. The method of claim 1, further comprising:
   determining the SRI value with an algorithm $$SRI = \frac{\{(T_{pos} - T_{sys})/(RR \text{ Interval} - T_{sys})\}}{E_{Ecc}}.$$

where $T_{pos}$ corresponds to the second time associated with the post-systolic strain peak, $T_{sys}$ corresponds to the first time associated with the systolic strain peak, $RR_{Interval}$ corresponds to a cardiac RR interval, and $E_{Ecc}$ corresponds to the early diastolic strain peak.

5. The method of claim 1, wherein the plurality of cardiac images are obtained from a magnetic resonance imaging machine.

6. The method of claim 1, wherein the plurality of cardiac images are obtained from an echocardiography device.

7. The method of claim 1, further comprising:
   determining a risk associated with heart failure based upon the SRI value.

8. The method of claim 1, further comprising:
   determining a risk associated with atrial fibrillation based upon the SRI value.

9. A device, comprising:
   one or more memories; and
   one or more processors, communicatively coupled to the one or more memories, configured to:

obtain, from an imaging modality, a plurality of cardiac images of a subject;

determine, from the plurality of cardiac images of the subject, a first time associated with a systolic strain peak, a second time associated a post-systolic strain peak, and an early diastolic strain peak;

compute a strain rate index (SRI) value using the first time associated with the systolic strain peak, the second time associated with the post-systolic strain peak, and the early diastolic strain peak, the SRI being computed based upon a difference between the first time associated with the systolic strain peak and the second time associated with the post-systolic strain peak divided by the early diastolic strain peak;

determine a level of risk of cardiac failure using the SRI value;

determine a treatment plan for the subject based on the level of risk of cardiac failure; and provide information associated with the level of risk of cardiac failure and the treatment plan for review by a medical professional.

10. The device of claim 9, where the one or more processors are further configured to:
assess cardiac deformation that precedes filling.

11. The device of claim 9, where the one or more processors are further configured to:
calculate a difference between a cardiac RR interval and the first time associated with the systolic strain peak when computing the SRI value.

12. The device of claim 9, where the one or more processors are further configured to:
determine the SRI value with an algorithm comprising $$SRI = \frac{\left\{\frac{(T_{pos} - T_{sys})}{(RR\ \text{Interval} - T_{sys})}\right\}}{E_{Ecc}},$$

where $T_{pos}$ corresponds to the second time associated with the post-systolic strain peak, $T_{sys}$ corresponds to the first time associated with the systolic strain peak, $RR_{interval}$ corresponds to a cardiac RR interval, and $E_{Ecc}$ corresponds to the early diastolic strain peak.

13. The device of claim 9, where the plurality of cardiac images are obtained from a magnetic resonance imaging machine.

14. The device of claim 9, where the plurality of cardiac images are obtained from an echocardiography device.

15. The device of claim 9, where the one or more processors are further configured to:
determine a heart failure based on the SRI value.

16. The device of claim 9, where the one or more processors are further configured to:
determine a risk of atrial fibrillation based on the SRI value.

17. A non-transitory computer readable medium storing instructions comprising:
one or more instructions that, when executed by one or more processors, cause the one or more processors to be configured to:

obtain, from an imaging modality, a plurality of cardiac images of a subject;

determine, from the plurality of cardiac images of the subject, a first time associated with a systolic strain peak, a second time associated with a post-systolic strain peak, and an early diastolic strain peak;

compute a strain rate index (SRI) value using information associated with the first time associated with the systolic strain peak, second time associated with the post-systolic strain peak, and the early diastolic strain peak, the SRI being computed based upon a difference between the first time associated with the systolic strain peak and the second time associated with the post-systolic strain peak divided by the early diastolic strain peak;

determine a level of risk of cardiac failure using the SRI value;

determine a treatment plan for the subject based on the level of risk of cardiac failure; and provide information associated with the level of risk of cardiac failure and the treatment plan for review by a medical professional.

18. The non-transitory computer readable medium of claim 17, where the one or more instructions, when executed by the one or more processors, further cause the one or more processors to be configured to:
determine the first time associated with the systolic strain peak and the second time associated with the post-systolic strain peak using mid-wall ventricular circumferential strain associated with a cardiac cycle of the subject; and
determine the early diastolic strain peak using strain rates associated with the cardiac cycle of the subject.

19. The non-transitory computer readable medium of claim 17, where the one or more instructions, when executed by the one or more processors, further cause the one or more processors:
determine the SRI value with an algorithm comprising $$SRI = \frac{\{(T_{pos} - T_{sys})/(RR\ \text{Interval} - T_{sys})\}}{E_{Ecc}},$$

where $T_{pos}$ corresponds to the second time associated with the post-systolic strain peak, $T_{sys}$ corresponds to the first time associated with the systolic strain peak, $RR_{Interval}$ corresponds to a cardiac RR interval, and $E_{Ecc}$ corresponds to the early diastolic strain peak.

20. The non-transitory computer readable medium of claim 17, where the one or more instructions, when executed by the one or more processors, further cause the one or more processors to be configured to:
calculate a difference between a cardiac RR interval and the first time associated with the systolic strain peak when computing the SRI value.

* * * * *